(12) United States Patent
Campana et al.

(10) Patent No.: US 8,219,354 B2
(45) Date of Patent: Jul. 10, 2012

(54) BOLUS FOR RADIOTHERAPY AND METHOD FOR DETERMINING THE SHAPE OF SUCH A BOLUS

(75) Inventors: Francois Campana, Joinville (FR);
Jean-Yves Kristner, Fontenay (FR);
Jeremy Lachet, Malakoff (FR);
Nathalie Fournier-Bidoz, La Celle les Bordes (FR)

(73) Assignee: Institut Curie, Paris (FR)

( * ) Notice: Subject to any disclaimer, the term of this patent is extended or adjusted under 35 U.S.C. 154(b) by 408 days.

(21) Appl. No.: 12/528,935

(22) PCT Filed: Feb. 27, 2008

(86) PCT No.: PCT/FR2008/050332
§ 371 (c)(1),
(2), (4) Date: Aug. 27, 2009

(87) PCT Pub. No.: WO2008/119905
PCT Pub. Date: Oct. 9, 2008

(65) Prior Publication Data
US 2010/0070236 A1    Mar. 18, 2010

(30) Foreign Application Priority Data
Feb. 27, 2007    (EP) .................................. 07290246

(51) Int. Cl.
*G01B 5/20* (2006.01)
(52) U.S. Cl. ....................................................... 702/167
(58) Field of Classification Search .................. 702/167
See application file for complete search history.

(56) References Cited

U.S. PATENT DOCUMENTS

| 5,120,816 A | 6/1992 | Gould et al. | |
| 6,191,216 B1 * | 2/2001 | Ganster et al. | 524/779 |
| 6,231,858 B1 * | 5/2001 | Izeki et al. | 424/1.69 |

FOREIGN PATENT DOCUMENTS

| EP | 0 928 795 | 7/1999 |
| FR | 2 682 289 | 4/1993 |

OTHER PUBLICATIONS

Perkins M.D., "A Custom Three-Dimensional Electron Bolus Technique for Optimization of Postmastectomy Irradiation," Int. J. Radiation Oncology Biol. vol. 51, No. 4. Nov. 2001, pp. 1142-1151.
Kudchadker, "Utilization of custom electron bolus in head and neck radiotherapy," Journal of Applied Clinical Medical Physics, vol. 4, No. 4, Fall 2003, pp. 312-333.

* cited by examiner

*Primary Examiner* — Cindy H Khuu
(74) *Attorney, Agent, or Firm* — Greer, Burns & Crain, Ltd.

(57) ABSTRACT

A bolus that is intended to be irradiated during radiotherapy. Advantageously, the bolus is made from a polyurethane gel.

5 Claims, 4 Drawing Sheets

BOLUS FOR RADIOTHERAPY AND METHOD FOR DETERMINING THE SHAPE OF SUCH A BOLUS

BACKGROUND

The present invention relates to a bolus intended to receive irradiation during radiotherapy. It has a particularly useful but non-limitative application in breast radiotherapy.

By bolus is meant a material, if possible tissue-equivalent, placed in the contact with an irradiated region in order to correct surface irregularities or in order to give to the depth dose distribution a shape appropriate for the anatomical structures to be protected or irradiated.

In general, radiotherapy is becoming unavoidable in the treatment of breast cancers, regardless of the stage of development of the tumor and the therapeutic protocol; it limits the risk of local recurrence by 70%. Thus, radiotherapy is indispensable in radical surgery where a mastectomy combined with axillary curage is followed by irradiation of the thoracic wall and the drainage lymph node areas. It is becoming essential with the development of conservative treatments, surgery being limited to a tumorectomy and axillary curage. In other words, radiotherapy is indispensable in all forms of breast cancer in particular, usually combined with surgery and sometimes with chemotherapy.

In France, 50% of radiotherapy treatments after mastectomy use electron beam irradiation.

Treatment consists of irradiating a target volume which can be:
  the breast or the thoracic wall,
  the axillary region,
  the supraclavicular region,
  the internal mammary chain.

The problem associated with irradiation is therefore the presence of healthy organs in close proximity to the target to be treated. Irradiation of these healthy organs must be avoided, which can for example comprise:
  the lungs,
  the heart,
  the brachial plexus,
  the cervical spinal cord,
  the larynx, or
  the thyroid.

FIG. 1 according to the prior art shows a curve representing the energy efficiency of an electron beam irradiation as a function of the depth (Z) in the body. Physical phenomena mean that the efficiency does not follow a linear decrease from the skin to the inside of the body. Instead the efficiency has a dose maximum at a certain depth relative to the skin and then rapidly decreases exponentially. In most cases, it is necessary to shift this maximum so that the latter is situated exactly on the target while providing maximum protection to the healthy organs. In FIG. 1 for example the dose maximum is at a depth of 20 mm. In order to carry out a shift, current practice consists of placing a bolus on the zone to be treated so as to artificially increase the thickness of the skin and thus reduce the depth of penetration of the irradiation beam. The bolus most commonly used is made of silicone sold in sections ranging from 5 to 10 mm thick. This silicone bolus is difficult to handle and remains expensive. FIG. 2 according to the prior art shows such a bolus placed on a body the surface of which has an irregular shape. Because of the relative rigidity of silicone, gaps 3, 4 and 5 form between the body 2 and the bolus 1. Moreover, it is clearly evident that the penetration of the electron beam is not homogeneous. The disadvantages of a silicone bolus are therefore essentially:
  difficulty in handling,
  a density other than 1, this silicone bolus is not tissue-equivalent,
  high cost, and
  available in sections of a fixed thickness, which does not allow it to fit properly to the irregular surface of a human body: this leads to inhomogeneity in the dose distribution in the target volume.

Document U.S. Pat. No. 6,231,858 is known which describes a bolus for radiotherapy constituted by an aqueous gel. This gel is prepared from a mixture of natural organic polymers and water. This bolus is inexpensive and can be adapted so as to correct the dose distribution. However, to produce this bolus it is necessary to heat the water to a temperature between 70 and 100° C. before incorporating a natural organic polymer into it. This high-temperature preparation method is very restrictive and requires permanent and rigorous monitoring in order to avoid in particular the presence of air bubbles.

The article "Utilization of custom electron bolus in head and neck radiotherapy" by Kudchadker et al. (Journal of Applied Clinical Medical Physics, pp. 322-333, Vol. 4, number 4, Fall 2003) describes a conformational wax bolus for radiotherapy treatment of the head and neck tumors. Two boluses were designed from data generated by a TPS (Treatment Planning System). The boluses were machined from modelling wax with an approximate density of 0.92 gm/cm$^3$ (p. 324, C).

The article by Perkins et al. "A custom three dimensional electron bolus technique for optimization of post-mastectomy irradiation" Int. J. Radiat. Oncol. Biol. Phys. 51, 1142-1151, describes the use of a compensating wax bolus in the radiotherapy of breast tumors. The authors describe the use of a wax bolus 3 to 4 cm thick and the application of 16 MeV of energy.

Moreover, in fields far removed and independent of radiotherapy, polyurethane-based materials are known for various applications.

Document FR 2 682 289 describes a heat- or cold-energy accumulator constituted by a polyurethane or silicone gel in a very flexible casing (p. 1., l. 31). This casing is necessary for the accumulator because one of the properties of the gel in general is that it is sticky (p 1., l. 31-33) and the cross-linking of the initial liquid components of the gel is easier in a casing.

Document U.S. Pat. No. 6,191,216 describes hydrophilic and self-adhesive polyurethane gel substances.

Document U.S. Pat. No. 5,120,816 describes polyurethane resins characterized by increased strength. The applications of these resins are in particular the manufacture of intravenous catheters (col. 1, l 9-53). U.S. Pat. No. 5,120,816 also describes, among other objects manufactured with such a resin, boluses for animals (col. 14, l. 9). The description (p. 10, l. 30-35) refers to boluses for animals such as cattle or sheep where the property of the increased strength of the polyurethane resin is important. Thus "bolus" is a medical term also denoting an intravenous injection of a significant dose of a therapeutic agent. The term "bolus" in document U.S. Pat. No. 5,120,816 is therefore different from the bolus as treated in the present invention, which is a tissue-equivalent material to even out a dose of irradiation.

SUMMARY

The purpose of the present invention is to remedy as many of the abovementioned disadvantages as possible by proposing a novel bolus composition for radiotherapy.

The purpose of the present invention is in particular a novel bolus which is easy to manufacture and inexpensive.

Another purpose of the invention is a bolus that is easy to shape and can tolerate very fine cutting and is not simply a stack of layers.

At least one of the abovementioned objectives is achieved with a bolus intended to receive irradiation during radiotherapy. According to the invention, this bolus comprises polyurethane gel. The bolus according to the present invention can be designed simply. In fact, polyurethane gel is a material made from a mixture of two components at ambient temperature and normal pressure. Hardening is carried out cold, there is therefore no heating and no contraction effect. It is therefore simple to use a mould.

In contrast, the bolus described in document U.S. Pat. No. 6,231,858 is complex to implement, in particular by heating to a temperature between 70 and 100°.

Moreover, the polyurethane gel according to the invention is an inexpensive material which is cheaper than silicone for example.

The invention is remarkable in particular in that polyurethane gel is a material which is frequently used in the construction industry, in making car seats, in the soles of shoes or also in health equipment to absorb low-intensity shocks. Its extensive use in mechanics is explained in particular by its low cost.

Documents FR 2 682 289, U.S. Pat. Nos. 6,191,216 and 5,120,816 do not describe or suggest a bolus intended to receive irradiation during radiotherapy and comprising polyurethane gel. Radiotherapy is a well-defined technical field in which irradiation is used to destroy tumoral cells in a targeted manner while wishing to protect peripheral healthy tissue. The use of a polyurethane gel in radiotherapy was not obvious to a person skilled in the art particularly as polyurethane is a well-known and long-used material; similarly radiotherapy methods have been known for a long time.

The articles by Kudchadker and Perkins according to the prior art do not describe or suggest a bolus for radiotherapy comprising polyurethane gel. A bolus comprising polyurethane gel according to the invention is flexible and has self-adhesive properties, its thickness can be limited and it is possible to adjust its density in a precise manner. Moreover, it can be manufactured easily by moulding. Unlike a rigid wax bolus as described in the prior art, a bolus according to the invention does not necessarily need fixing means (adhesive) to be used to keep it in place during treatment. Because of its self-adhesive properties, the bolus can also be positioned, at least partially, on the side of the patient. Its flexibility and lightness make it more comfortable for the patient. According to the invention, the irregularity of a surface to be treated can be evened out, for example after a mastectomy.

The polyurethane gel according to the invention advantageously has a density approximately equal to 1 which avoids any problems associated with the bolus-body transition. A tissue-equivalent bolus is obtained.

The bolus is advantageously constituted by a polyurethane gel composed of a mixture of polyol and isocyanate, the latter being able to be aliphatic or aromatic.

According to an advantageous feature of the invention, the polyurethane gel comprises at most fifteen per cent isocyanate, preferably between five and fifteen per cent. More precisely, this polyurethane gel comprises approximately eight to ten per cent isocyanate and ninety-two to ninety per cent polyol. Such a distribution allows a polyurethane gel to be obtained which is easy to work, with ideal elasticity, hardness and stickiness.

According to an advantageous feature of the invention, this bolus is intended to be stuck to the body. It has a shape which makes it possible to place approximately the dose maximum in a predefined target within said body. The texture of the polyurethane gel according to the invention makes it possible to produce very fine details. It is easy to mould and cut.

The bolus according to the invention makes it possible to ensure a compensating function vis-à-vis irradiation and makes it possible to have homogeneous irradiation over the whole of the target.

According to a preferred embodiment of the invention, the shape of the bolus is such that the bolus fits perfectly to the surface of the body and the thickness of the target-and-bolus unit is approximately the same over all of the zone to be treated.

According to another feature of the invention, a method is proposed for determining the shape of a bolus according to the present invention, this bolus being intended to receive irradiation during radiotherapy. The method advantageously comprises the following steps:

determination of a first volume defining a deep part of the target to be irradiated within said body, determination of a second volume by three-dimensional expansion of said first volume, at least one part of the second volume being on the outside of the body, determination of the shape of the bolus, this shape being the part of the second volume located on the outside of the body.

Three-dimensional expansion is a known technique in which an algorithm is used as defined in particular in the following publications:

R. Belshi, D. Pontvert, J. C. Rosenwald, and G. Gaboriaud, "Automatic three dimensional expansion of structures applied to determination of Clinical Target Volume in conformal radiotherapy," Int. J. Rad. Oncol. Biol. Phys., vol. 37, pp. 689-696, 1997; or J. C. Stroom and P. R. M. Storchi, "Automatic calculation of three-dimensional margins around treatment volumes in radiotherapy planning," Phys. Med. Biol., vol. 42, pp. 745-755, 1997.

Three-dimensional expansion is advantageously carried out until the thickness between the first volume and the second volume is approximately constant over the whole of the target.

Three-dimensional expansion can also be carried out until the contour of the second volume is approximately touching the surface of the target at one point, this point of contact being situated in the thickest zone of the target such that the extended volume encompasses all of the target and even includes an external volume, that of the bolus in this case.

The bolus is then advantageously produced by moulding, in particular cold-moulding, at ambient temperature. A bolus according to the invention can therefore be manufactured easily and is reproducible by moulding, while a wax bolus according to the prior art requires double machining (internal/external).

Other advantages and characteristics of the invention will become apparent on examination of the detailed description of an embodiment which is in no way limitative, and the attached drawings in which:

DETAILED DESCRIPTION

Although the invention is not limited by it, a bolus will now be described which is used as a compensator during radiotherapy by electron beam irradiation.

By way of example, in order to treat breast cancer it may be necessary to carry out a mastectomy consisting of complete surgical removal of a breast.

Figure 1:
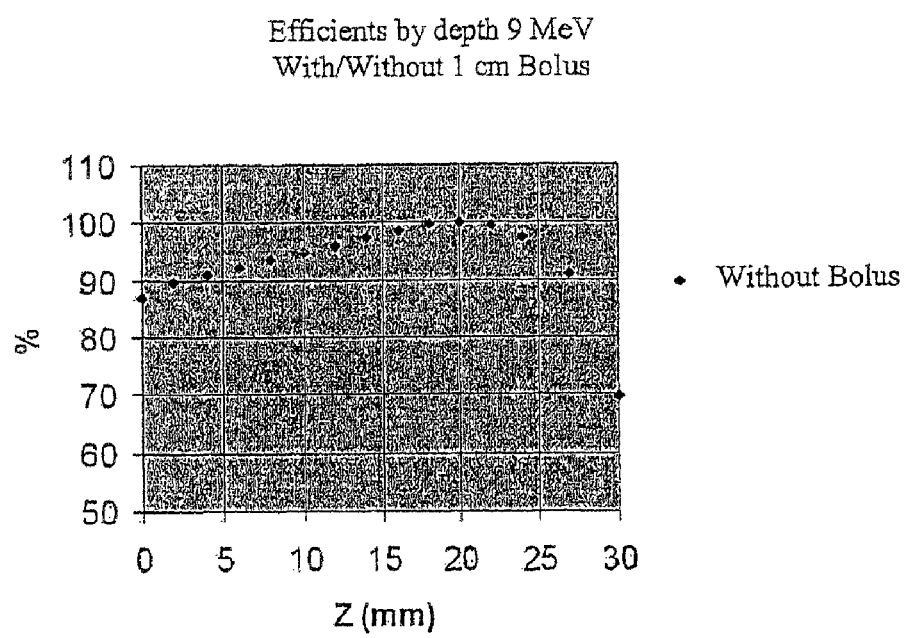
FIG. 1 is a graph illustrating the efficiency of an electron beam dose as a function of the distance of penetration into a human body, according to the prior art.
Figure 2:
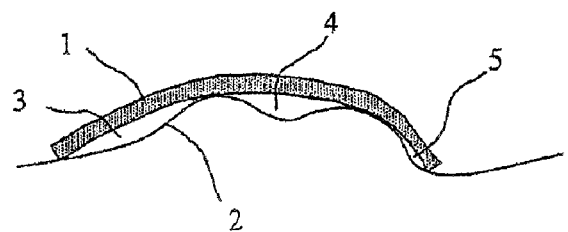
FIG. 2 is a diagrammatic cross section view of a bolus according to the prior art placed on a breast before being irradiated for radiotherapy treatment.
Figure 3:
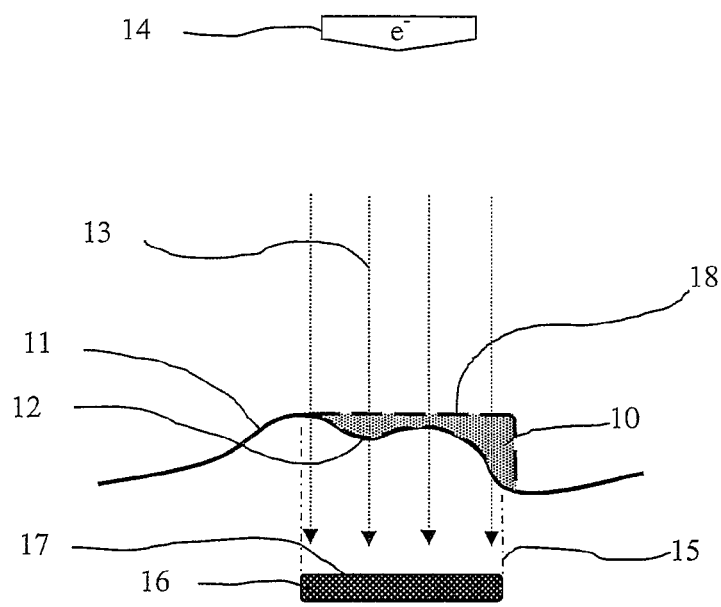
FIG. 3 is a diagrammatic cross section view of a bolus according to the present invention placed on a volume during radiotherapy.
Figure 4:
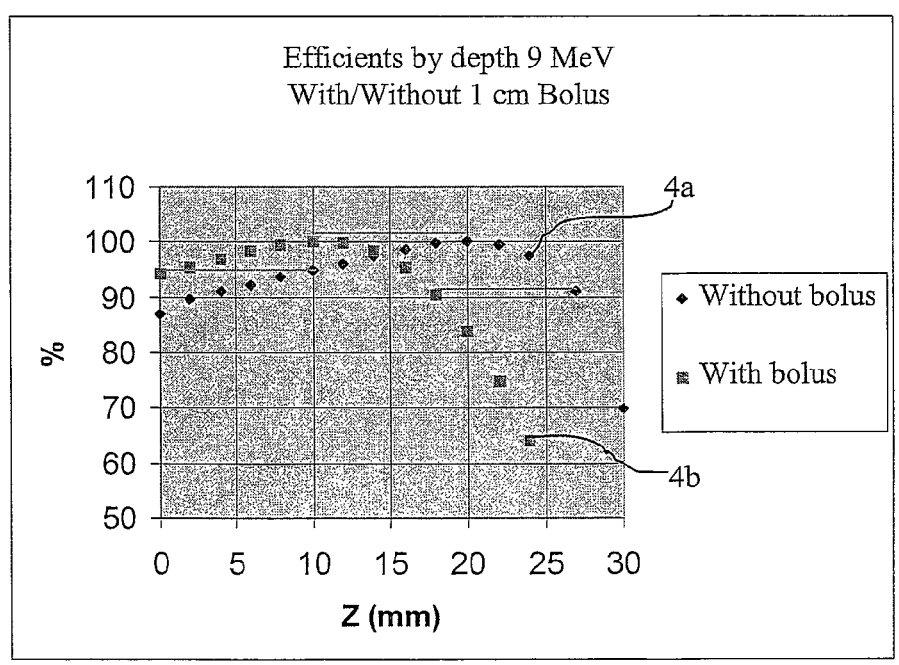
FIG. 4 is a graph illustrating the efficiency of an electron beam dose as a function of the distance of penetration into a human body, in the presence (4b) and in the absence (4a) of a bolus according to the present invention.

The bolus according to the present invention is designed starting from a polyurethane gel comprising a mixture of 90 per cent polyol and 10 per cent isocyanate. It has a density of 1. The fluidity of this polyurethane gel allows very fine modelling to be carried out. FIG. 3 shows a volume 11 with a hollow 12 following a surgical operation. The target 15 is located between the skin (limit of the volume 11) and lung (16). The treatment consists of electron beam irradiation 13 from a source 14. The dotted lines delimit the target 15 which is the volume of the body undergoing treatment. The bolus 10 according to the present invention advantageously has a three-dimensional shape such that the paths of the rays of the electron beam 13 pass through the treatment volume 15 to approximately the same depth. In other words, the distance between the surface 18 of the bolus 10 and the surface 17 of the lung 16 is approximately the same over the whole of the volume to be treated. The bolus 10 was made from polyurethane gel, then modelled so as to fit perfectly to the outside surface of the breast 11. FIG. 4 shows a graph illustrating two efficiency curves 4a and 4b as a function of the depth of penetration of the electron beam for a source of 9 MeV electrons and for a 1 cm bolus. The curve 4a corresponds to an efficiency without a bolus according to the present invention. The curve 4b corresponds to an efficiency with a bolus 1 cm thick according to the present invention. Thanks to a density equal to 1, it can be seen advantageously that the curve 4b underwent a translation of 1 cm relative to the curve 4a, the maximum is therefore also displaced by 1 cm.

A bolus of 1 cm according to the invention causes a shift of 1 cm. This maximum is achieved for a depth of 10 mm, then the curve decreases rapidly. As a result, with the bolus according to the present invention, a bolus can be designed having an appropriate shape so that the maximum efficiency is situated at the level of the target to be irradiated, which allows the healthy organs close to the target, such as the lung, to be protected.

Figure 5:
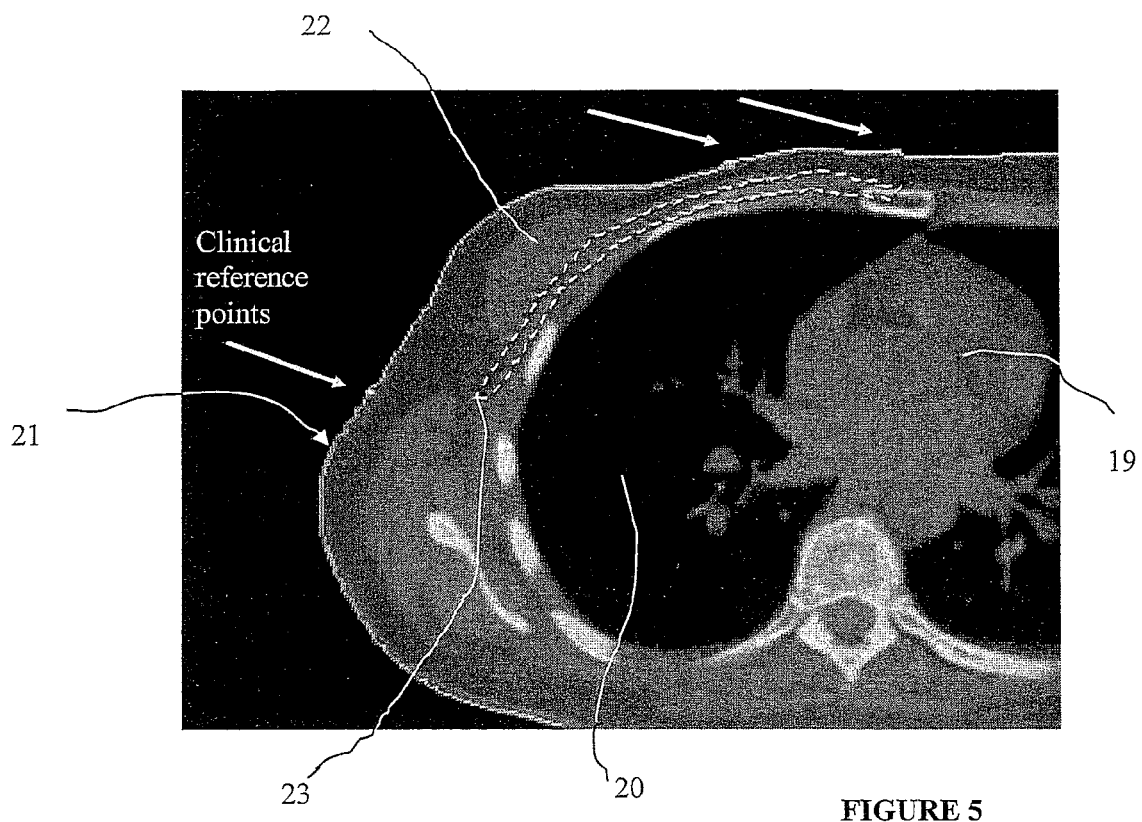
FIGS. 5 to 7 are simplified views illustrating the different steps for determining the shape of a bolus according to the present invention.
Figure 6:
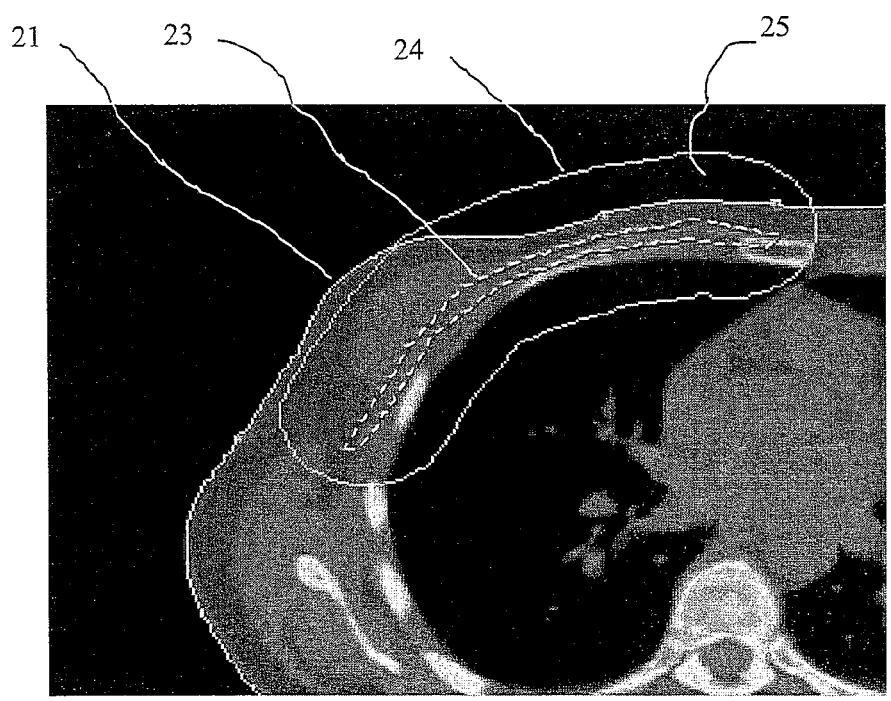
Figure 7:
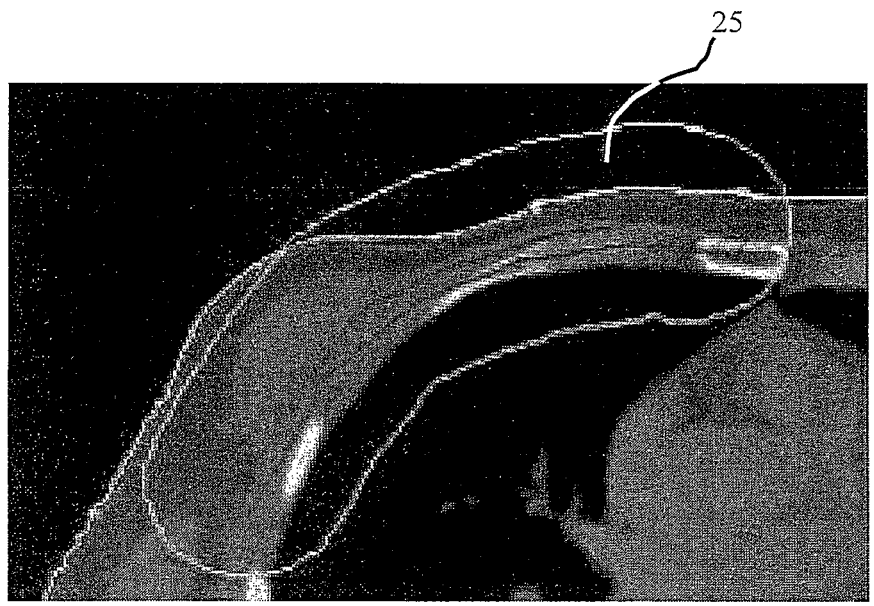

FIGS. 5 to 7 show the different steps for producing a compensating bolus which allows the thicknesses crossed between the entry surface and the rear side of the target volume (costal wall) at each section level to be equalized. FIG. 5 is a cross section view of a body at the level of the thorax. It shows the heart 19 and a lung 20 which are the organs to be protected against the electron radiation. To start with, the outside wall 21 of the thorax 22 is defined by using, in particular, clinical reference points in the form of metal spheres on the skin. A first volume 23, which represents the deep part of the volume to be irradiated, is then defined. This first three-dimensional volume is located in the thorax. The bolus must be produced so that the dose distribution between the skin and the volume 23 is comprised between 90 and 100%.

Figure 8:
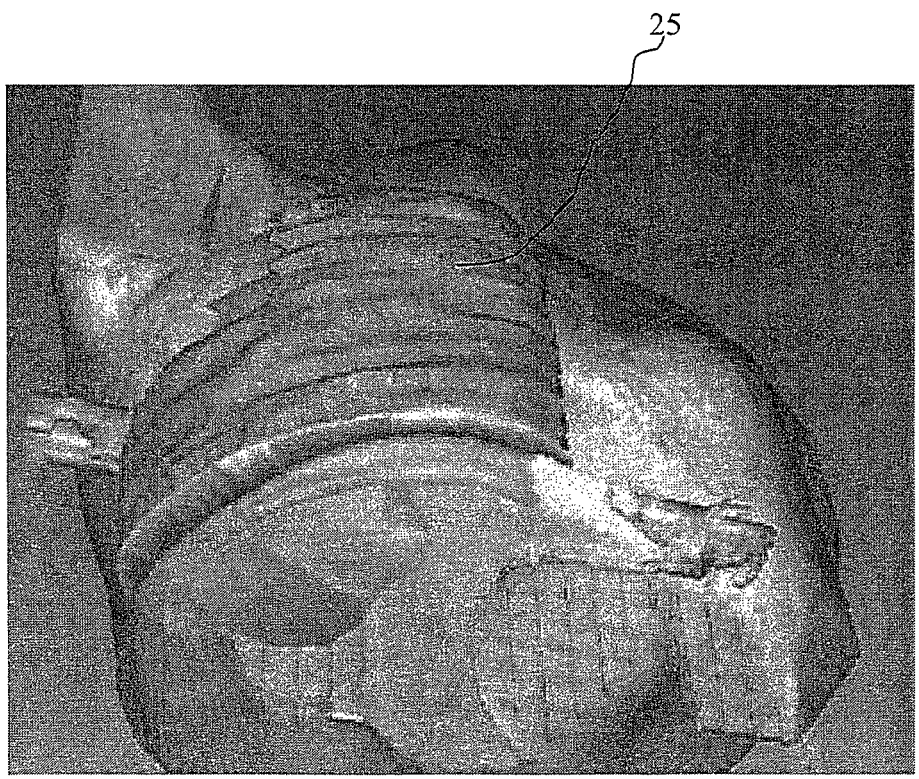
FIG. 8 is a three-dimensional view of a bolus obtained following the steps described in FIGS. 5 to 7.

In FIG. 6, the first volume 23 is expanded in order to generate a second volume 24. For example, expansion is carried out until a smooth surface is obtained on the section of maximum thickness. This expansion can advantageously be carried out using computer equipment. Once the expansion is completed, a third volume 25 is determined which is outside the thorax 22 and delimited by the contour of the second volume 24 and the contour of the thorax 21. This third volume 25 represents the dimensions of the bolus to be designed. A precise delimitation of the bolus is carried out on FIG. 7 and FIG. 8 is a three-dimensional representation of the bolus on the thorax to be treated.

The thickness of a bolus according to the invention is preferably less than or equal to 1 cm; the energy of the electrons which must be applied is less significant than when the bolus has a thickness of 3 to 4 cm as described in the prior art. The use of a bolus according to the invention makes it possible, for example, to apply energy that is less than or equal to 12 MeV, thus limiting the risks of complications associated with a high dosage at the cutaneous level and in other tissues or organs.

Compared with a silicone or wax bolus according to the prior art, the density of the polyurethane gel of the bolus according to the invention can be adjusted precisely and homogeneously to preferably attain a density very close or equal to 1 gm/cm$^3$, the bolus can therefore be perfectly similar to skin in order to calculate the administered doses. The density of the silicone cannot be homogeneous and is slightly greater than 1 gm/cm$^3$. The density of the wax is less than 1 gm/cm$^3$ (cf. Kudchadker et al.).

A bolus according to the invention can have the appearance of a polyurethane gel plate of variable dimensions. The dimensions of the plate can be, for example, 30 cm×30 cm, for a thickness preferably comprised between 0.5 and 1 cm. This plate can have recesses, for example to make it possible to adapt it to the right or left side of the patient. In a particular embodiment, a bolus according to the invention has a bevelled edge or edges so as to avoid an "edge effect" or "dose attenuations" for tissues situated under the edges of the plate.

The indentations and bevelled edges of the plates can be obtained either directly during the moulding by pouring the polyurethane gel into a suitable mould or by cutting the plate after moulding.

A bolus according to the invention can also have the appearance of a plate the thickness and the contours of which are determined according to the patient's own parameters.

A bolus according to the invention can be composed of several plates and comprise, for example, a stack of plates, with a "standard" plate combined with a plate the dimensions of which are appropriate for the patient. The plates are preferably bevelled so as to avoid dose heterogeneity at the transition between the different thicknesses of the bolus.

A bolus according to the invention can comprise, in addition to the polyurethane gel, at least one additive which makes it possible to improve its properties to the extent that the presence of this additive does not modify the desired density properties for the radiotherapy envisaged. In particular, a bolus according to the invention can comprise at least one additive having the effect of increasing its resistance to washing, disinfection and/or sterilization, such as for example gamma irradiation applied for sterilization. A bolus according to the invention can also comprise at least one additive having the effect of improving its resistance to tearing at thin edges. These additives can be antioxidants or others as mentioned in document U.S. Pat. No. 6,191,216.

The invention also relates to moulds for producing the boluses comprising polyurethane gel according to the invention. The mould required to produce the bolus by pouring the gel can be obtained after exporting an electronic "volume" file edited using a TPS (Treatment Planning System) tool to a digital machining centre.

For example, such a mould can be made in two parts in a low-density machinable block. Such a mould makes it possible to pour the polyurethane gel directly.

Of course, the invention is not limited to the examples which have just been described and numerous adjustments can be made to these examples without exceeding the scope of the invention. In fact, the present invention can be used for irradiation other than electron beam irradiation, such as for example gamma radiation or X radiation. Moreover, the production of a volume bolus can be envisaged which is then cut very finely in order to adapt the bolus according to target.

The invention claimed is:

1. A method for determining a shape of a bolus comprising polyurethane gel, the bolus being molded by a molding machine and used for compensating irradiation during a radiotherapy, the method comprising the following steps:
    determining, by a computer, of a first volume defining a part of a target to be irradiated within a body;
    determining of a second volume by three-dimensional expansion of said first volume, at least one part of said second volume being on the outside of the body; and
    determining of the shape of the bolus as being the part of said second volume located on the outside of the body.

2. The method according to claim 1, wherein the three-dimensional expansion is carried out until the thickness between said first volume and said second volume is approximately constant over all of the target.

3. The method according to claim 1, wherein the three-dimensional expansion is carried out until the contour of said second volume is approximately touching the surface of the target at one point, this point of contact being situated in the thickest zone of the target.

4. The method according to claim 1, wherein the bolus is prepared by molding.

5. The method according to claim 4, wherein the moulding is carried out at room temperature.

* * * * *